United States Patent [19]

Feighner et al.

[11] Patent Number: 5,350,763
[45] Date of Patent: Sep. 27, 1994

[54] UNGUINOL AND ANALOGS ARE ANIMAL GROWTH PERMITTANTS

[75] Inventors: Scott D. Feighner, Westfield; Gino M. Salituro, Fanwood; Jack L. Smith, Colonia; Nancy N. Tsou, Westfield, all of N.J.

[73] Assignee: Merck & Co., Inc., Rahway, N.J.

[21] Appl. No.: 75,253

[22] Filed: Jun. 11, 1993

[51] Int. Cl.$^5$ .................. A61K 31/365; C07D 321/10
[52] U.S. Cl. .................................. 514/450; 549/267; 549/268; 549/349
[58] Field of Search ...................... 549/268, 349, 267; 514/450

[56] References Cited

PUBLICATIONS

Sierankiewicz, et al, Acta Chemica Scandinavia 26 pp. 455–458 (1972).
Kawakara, et al, Chem Pharm Bull 36 pp. 1970–1975 (1988).
Stodula, et al, Phytochem 11, pp. 2107–2108 (1972).
Hamaro, et al, J. Antibiotics pp. 1195–1201 (1992).

*Primary Examiner*—C. Warren Ivy
*Assistant Examiner*—Ba K. Trinh
*Attorney, Agent, or Firm*—David L. Rose; Joseph F. DiPrima

[57] ABSTRACT

Unguinol is a well-known metabolite of the fungi *Aspergillus unguis* and *Aspergillus nidulans*. Unguinol has been found to be an active growth permittant and promotant in animals, in particular, monogastric animals such as chickens. In addition, the fermentation broth also produced the additional known unguinol derivatives of folipastatin and 2-chloro unguinol as well as the novel 4-methyl derivative. All of these compounds are active animal growth permittants. Compositions containing such unguinol derivatives for use as growth permittants and promotants are also disclosed.

7 Claims, No Drawings

UNGUINOL AND ANALOGS ARE ANIMAL GROWTH PERMITTANTS

BACKGROUND OF THE INVENTION

Unguinol is a known metabolite of various fungi and is also referred to as Yasimin and tris dechloronornidulin. See Sierankiewicz et al in *Acta Chim. Scan* 26 pg. 455–458(1972) describing the preparation of unguinol from *Aspergillus nidulans;* and Kawakara et al in *Chem Pharm Bull* 36 pg. 1970–1975 (1988), Kawakara et al in *J. Chem Soc* Perkins Trans I pg 2611–2614(1988), and Stodola et al in *Phytochem* 11 pg 2107–2108(1972) describing the preparation of unguinol and analogs thereof from *Emeticella unguis*. No utilities are given in the foregoing references. No suggestions are made that unguinol could be used as an animal growth permittant.

DESCRIPTION OF THE INVENTION

Unguinol and the following analogs have been recovered from the fermentation of *Aspergillus unguis* and they have the following structures:

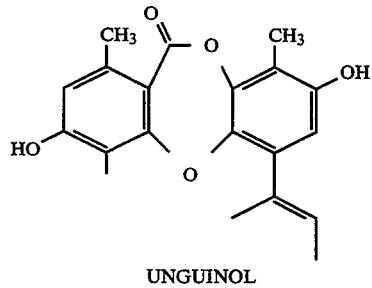

UNGUINOL

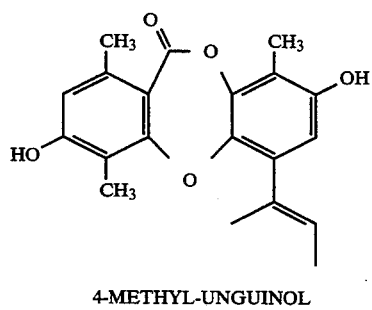

4-METHYL-UNGUINOL

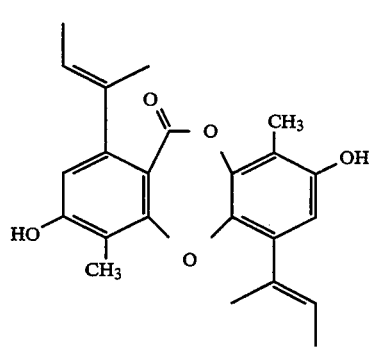

FOLIPASTATIN

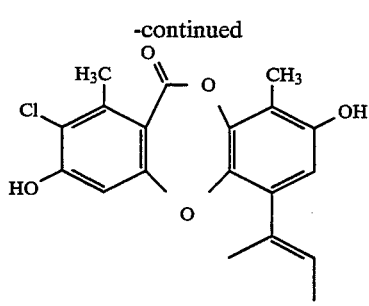

2-Cl-UNGUINOL

In accordance with this invention, the above compounds, with growth permittant activity, are described, which are prepared by growing, under controlled conditions with a culture of the microorganism *Aspergillus unguis* strain MF-141. The compounds are obtained by fermentation and recovered in substantially pure form as described herein.

In addition to the above known compounds, the extraction and recovery steps carried out on the fermentation broth of *Aspergillus unguis* recovered the following novel compound, specifically 4-methyl unguinol.

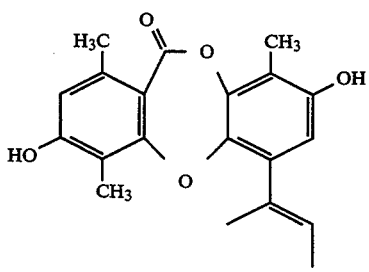

4-METHYL-UNGUINOL

4-Methyl unguinol has been identified as a novel derivative of unguinol by comparing its isolation characteristics and its analytical properties with known unguinol derivatives. The nuclear magnetic resonance $^{13}C$ spectrum of 4-methyl unguinol afforded the following peaks in $CD_3OD$: (given in $\delta$ (ppm)) 166.3, 163.6, 161.5, 153.8, 148.0, 143.3, 142.4, 137.5, 135.8, 126.3, 116.3, 115.4, 114.9, 113.6, 112.6, 21.1, 18.3, 14.1, 9.4 and 9.1. The proton chemical shifts of 4-methyl unguinol in $CD_3OD$ are as seen in the following Table:

| $\delta$ (ppm) | Multiplicity |
| --- | --- |
| 6.51 | s |
| 6.37 | s |
| 5.51 | qq |
| 2.33 | s |
| 2.13 | s |
| 2.11 | s |
| 2.03 | s |
| 1.77 | dd |

Based upon the foregoing data, the structure of the metabolite is confirmed as being 4-methyl unguinol, which structure has not previously been described.

The culture of *Aspergilis unguis* designated MF-141 is in the culture collection of Merck & Co., Inc., Rahway, N.J. A sample of this culture, capable of producing the herein described compounds is available in the permanent culture collection of the American Type Culture Collection at 12301 Parklawn Drive, Rockville, Md. 20852, deposited as a patent deposit under the Budapest Treaty for the Deposit of Microorganisms for Purposes of Patent procedure on Sep. 30, 1992 and has been assigned the accession number ATCC 74188.

The cultural characteristics of *Aspergillus unguis* MF-141 are as follows:

Colonies on Blakeslee's malt sugar (malt extract 20 g, peptone 1 g, glucose 20 g, agar 15 g, dH$_2$O 1000 mL) at 25° C., 12 hour photoperiod, growing relatively slowly, attaining 10–12 mm diameter in 1 week, at 37° C. in darkness growing more rapidly, attaining a diameter of 22–24 mm. Colonies slightly raised, dry, dull, in age appearing minutely pruinose at colony surface because of development of sterile hyphal spicules, translucent to pale green at margin, soon becoming uniformly dull, drab green, Sage Green, Artemesia Green (capitalized color names from Ridgway, R. 1912. *Color Standards and Nomenclature*, Washington, D.C), margin even, slightly submerged, reverse pale greenish yellow.

Colonies on cornmeal agar (Difco Laboratories) at 25° C., 12 hour photoperiod, growing relatively slowly, attaining a diameter of 12–15 mm, dull, dry, with more sparse development of conidial heads, pale translucent-green to dull green, pale translucent green in reverse.

Colonies growing at 25° C., 12 hour photoperiod on media with high osmolarity, G25N (K$_2$PO$_4$ 0.75 g, NaNO$_3$ 3 g, KCl 0.5 g, MgSO$_4$.7H$_2$O 0.5 g, FeSO$_4$.7H$_2$O 0.01 g, yeast extract 3.7 g, glycerol 250 g, agar 12 g, dH$_2$O 750 mL; Pitt, J. I. 1979. *The Genus Penicillium and its Teleomorphic States Eupenicillium and Talaromyces.* Academic Press, London) attaining 10–15 mm diameter, dull, dry, bright yellow to dull greenish yellow in age, Pale Lemon Yellow, Light Cadmium, Lemon Chrome, Citrine, dull grayish yellow in reverse.

Conidial heads predominantly biseriate, columnar, slightly twisted in age, translucent to pale green at the base, becoming dull green. Conidiophores 80–150 μm tall, 4–6.5 μm wide, straight to fleruous, often attenuated toward base, flaring toward vesicle, arising from foot cells, with walls smooth, slightly thickened, pale yellowish brown to pale olivaceous brown in KOH. Vesicles 9–12 μm in diameter, subclavate to hemispherical, with metulae restricted to the upper 50%. Conidiogenous cells phialidic, arising from metulae in groups of 1–4, usually 3,3–4×2–3.5 μm, cylindrical to ampulliform, with distal end tapered to broadly truncate. Metulae broadly cylindrical to clayate, 4.5–6×3–4.5 μm. Conidia 3–4 μm in diameter, globose to subglobose, minutely echinulate or roughened, hyaline to grayish green in KOH, adhering in chains by colorless connectives. Hyphae septate, smooth, highly branched. Erect hyphal spicules formed in mature colonies, up to 1200 μm tall, 3–5 μm wide, resembling sterile conidiophores, with tapered to acute apices, with walls slightly thickened. Hulle cells, sclerotia or cleistothecia not observed.

This isolate is assigned to the *Aspergillus nidulans* group (K. B. Raper & D. I. Fennell. 1965. *The Genus Aspergillus.* Williams & Wilkins, Baltimore) based on the combination of: biseriate, columnar conidial heads; smooth, pigmented conidiophores; hemispherical vesicles; toughened globose conidia; and drab green colony colors. Within the *A. nidulans* group, *A. unguis* is immediately distinguished from all other species by the presence of sterile hyphal spicules that develop among conidiophores in mature colonies. This isolate was not observed to form cleistothecia, however some strains of *A. unguis* may form cleistothecia. This state of the lifecycle has been named *Emericella unguis* Malloch & Cain.

The above-mentioned microorganism is illustrative of the strains of *Aspergillus unguis* which can be employed in the production of unguinol and its sec-butenyl analog. It is to be understood, however, that mutants of the above-mentioned organism, for example, those unguinol and sec-butenyl unguinol producing mutants that are obtained by natural selection or those produced by mutating agents including X-ray irradiation, ultraviolet irradiation, nitrogen mustard or like treatments also are included within the scope of this invention.

Unguinol and its derivative may be prepared during the aerobic fermentation of a producing strain of *Aspergillus unguis* MF-141 in either an agitated aqueous medium or in a static solid medium.

Where the nutrient medium is an aqueous medium, suitable media such as those used for the production of many antibiotic substances are suitable for use in this process for the production of unguinal and its sec-butenyl analog.

Such nutrient media contain sources of carbon and nitrogen assimilable by the microrganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, ingredients such as sugars, for example dextrose, sucrose, maltose, lactose, glycerol, or other sources of carbohydrates such as corn, millet, wheat, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount between 0.5 and 90% by weight of the medium is satisfactory. These carbon sources may be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, corn, millet, wheat, distillers solubles, cottonseed meal, meat extract and the like, are readily assimilable by *Aspergillus unguis* MF 141 in the production of the instant compound. The various sources of nitrogen can be used alone or in combination in amounts ranging from 0.2 to 95% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, cadmium, zinc, copper, and the like.

It should be noted that the media described hereinbelow and in the Examples are merely illustrative of the wide variety of media, which may be employed, and are not intended to be limitative.

The following are Examples of media suitable for growing strains of *Aspergillus unguis*.

| Medium A | |
|---|---|
| Dextrose | 10 g. |
| Soluble starch | 10.0 g. |
| Beef extract | 3.0 g. |
| Yeast autolysate (As ardamine pH available from Yeast Products, Inc., Clifton, N.J.) | 5.0 g. |
| NZ Amine-E (casein hydrolysate-available from Humko-Sheffield-Memphis, Tenn.) | 5.0 g. |
| $MgSO_4 \cdot 7H_2O$ | 0.05 g. |
| Phosphate Buffer | 2.0 ml |
| $CaCO_3$ | 0.5 g. |
| Distilled water | 1000 ml. |
| pH 7.0–7.2 | |
| Phosphate Buffer | |
| $KH_2PO_4$ | 91.0 g |
| $Na_2HPO_4$ | 95.0 g |
| Distilled water | 1000 ml |
| pH 7.0 | |
| Medium B | |
| Tomato paste | 20.0 g. |
| Primary yeast | 10.0 g. |
| Dextrin (CPC starch) | 20.0 g. |
| $CoCl_2 \cdot 6H_2O$ | 0.005 g. |
| Distilled water | 1000 ml. |
| pH 7.2–7.4 | |
| Medium C | |
| Corn meal | 20.0 g. |
| Distillers solubles | 10.0 g. |
| Soybean meal | 15.0 g. |
| Sodium citrate | 4.0 g. |
| $CaCl_2 \cdot 2H_2O$ | 0.5 g. |
| $MgSO_4 \cdot 7H_2O$ | 0.1 g. |
| $CoCl_2 \cdot 6H_2O$ | 0.01 g. |
| $FeSO_4 \cdot 2H_2O$ | 0.01 g. |
| Polyglycol P2000 (Polypropylene glycol mw 2000) | 2.5 mg. |
| Distilled water | 1000 ml. |
| pH 6.5 | |
| Medium D | |
| Lactose | 20.0 g. |
| Distillers solubles | 15.0 g. |
| Autolyzed yeast (Ardamine pH) | 5.0 g. |
| Distilled water | q.s. to 1000 ml |
| pH 7.0 | |
| Medium E | |
| Tomato paste | 40.0 g. |
| Oat Flour | 10.0 g. |
| Distilled water | 1000 ml |
| pH 7.0 | |
| Medium F | |
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard oil | 2.5 g. |
| Distilled water | 1000 ml. |
| pH 6.7 | |
| Medium G | |
| Dextrose | 10.0 g |
| Asparagine | 1.0 g |
| $K_2HPO_4$ | 0.1 g |
| $MgSO_4 \cdot 7H_2O$ | 0.5 g |
| Yeast Extract | 0.5 g |
| Oat Flour | 10.0 g |
| $CaCO_3$ | 3.0 g |
| Trace Element Mix | 10.0 ml |
| Distilled water | 1000 ml |
| Adjust pH to 7.2 | |
| Trace Element Mix | |
| $FeSO_4 \cdot 7H_2O$ | 1000 mg |
| $MnSO_4 \cdot 4H_2O$ | 1000 mg |
| $CuCl_2 \cdot 2H_2O$ | 25 mg |
| $CaCl_2 \cdot 2H_2O$ | 100 mg |
| $H_3BO_3$ | 56 mg |
| $(NH_4)_6MO_4O_{24} \cdot 6H_2O$ | 19 mg |
| $ZnSO_4 \cdot 7H_2O$ | 200 mg |
| Distilled water | 1000 ml |
| Medium H | |
| Medium G | 1000 ml |
| Oat Flour | 10 g |
| pH 7.2 | |

The fermentation employing *Aspergilis unguis* MF 141 can be conducted at temperatures ranging from about 20° C. to about 40° C. For optimum results, it is most convenient to conduct these fermentations at a temperature in the range of from about 20° C. to about 30° C. Temperatures of about 24°–26° C. are most preferred. The pH of the nutrient medium suitable for producing the instant compounds can vary from about 3.0 to 8.5 with a preferred range of from about 4.0 to 7.0.

Small scale fermentations are conveniently carried out by placing suitable quantities of nutrient medium in a flask employing known sterile techniques, inoculating the flask with either spores or vegetative cellular growth of *Aspergillus unguis* MF 141 loosely stoppering the flask with cotton and permitting the fermentation to proceed at a constant room temperature of about 25° C. on a rotary shaker at from 0 to 300 rpm for about 2 to 21 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Aspergillus unguis*. The fermentation is allowed to continue for from 5 to 20 days while agitating and/or aerating the nutrient medium at a temperature in the range of from about 20° to 28° C. The degree of aeration is dependent upon several factors such as the size of the fermentor, agitation speed, and the like. Generally the larger scale fermentations are agitated at about 95 to 300 RPM and about 2 to 20 cubic feet per minute (CFM) of air.

The fermentation of *Aspergillus unguis* is also successfully carried out in a solid fermentation medium under static, that is, non-agitated, conditions. The solid phase aerobic fermentation utilizes the same sources of carbon, nitrogen and inorganic salts as are used for the above-described submerged aqueous fermentation with the primary differences in the constitution of the medium being the quantity of water present. The solid phase fermentations constitute from 30 to 80% by weight of water. Where in comparison with a submerged fermentation medium which may utilize from 10 to 100 g of solid ingredients per liter of medium (1 to 10% w/v), a solid phase medium will contain from 20 to 70% w/v of the solid ingredients.

The solid phase fermentation may be carried out aerobically by maintaining a large ratio of surface area to the mass of the medium. This is readily accomplished by utilizing a 0.3 to 8 cm depth of medium in a fermentation tray or flask. Since the medium is not mechanically agitated, this ensures the presence of sufficient oxygen for growth. Alternatively the solid phase fermentation may be carried out in special trays fitted with sterile gauze for passing air through the solid medium or across the top thereof. Optionally the solid phase fermentation may be carried out with a tight fitting cover.

The fermentation of large scale portions of media may be carried out in stages of increasing quantities of media and it is not necessary that all of the stages be of the same type, that is aqueous or solid. It has been found to be preferable to carry out the initial stages of fermentation in aqueous media and transfer the media to larger scale solid media.

The compounds of this invention are found primarily in the mycelium on termination of the *Aspergillus unguis* fermentation and may be removed and separated therefrom as described below.

The separation of unguinol and its derivatives from the whole fermentation broth and the recovery of said compound is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compounds as well as other substances lacking the growth permittant activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the non-polar impurities, pass through. The column is washed with a moderately polar organic solvent such as methylene chloride or chloroform to further remove impurities, and is then washed with a mixture of methylene chloride or chloroform and an organic solvent of which acetonei methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, ion exchange resins, dextrans gels and the like, as the chromatographic medium, with various solvents and combinations of solvents as the eluent. Further purification can be accomplished by crystallization from appropriate solvents such as toluene, methylene chloride, chloroform, methanol, and the like. The use of the foregoing techniques as well as others known to those skilled in the art, will afford purified compositions containing the instant compound.

The compounds of this invention are useful as animal growth permittants and promotants.

The compounds of this invention can be used to increase the growth and feed efficiency of ruminant and non-ruminant animals such as sheep, cattle, goats, horses, swine, chickens and the like. The active compounds can be fed to the animal by incorporating them into the animal's feed or drinking water or they can be administered in a unit dosage form either orally as a drench, tablet, bolus or sustained release bolus or parenterally by injection or from a subcutaneous implant. The administration of the active compounds can produce a surprising increase in body weight, a decrease in body fat and an increase in body protein for the same food intake.

The active compounds can be administered to the animals at daily rates of from 0.001 to 10 mg/kg of body weight which may vary depending upon the particular animal being treated as well as the age and general physical condition of the animal. Preferably, daily dosages of from 0.01 to 1.0 mg/kg are utilized. When administered as part of the animal's feed or drinking water the active compound is present at rates from 0.01 to 100 ppm which is determined to provide the appropriate daily amounts of the growth promotant compound.

At the same dosages listed above for growth promotion effects, substantial increases in feed efficiency are also observed.

The method of improving the feed utilization of animals of this invention comprises orally administering to an animal an effective amount of one or more of the above-described compounds. Of course, the most economically important animals are cattle, sheep, goats, fowl and swine.

It has been found that the compounds of this invention increase the efficiency of feed utilization in animals. The easiest way to administer the compounds is by mixing them in the animal's feed. However, the compounds of this invention can be usefully administered in other ways. For example, they can be incorporated into tablets, drenches, boluses, or capsules, and dosed to the animals. Formulation of the compounds in such dosage forms can be accomplished by means and methods well known in the veterinary pharmaceutical art. Each individual dosage unit should contain a quantity of the feed-efficieny-improving compound which has a direct relation to the proper daily dose for the animal to be treated.

Capsules are readily produced by filling gelatin capsules with any desired form of the desired compound. If desired, the compound can be diluted with an inert powdered diluent, such as a sugar, starch or purified crystalline cellulose, in order to increase its volume for convenience in filling capsules.

Tablets of the compounds useful in this novel method are made by conventional pharmaceutical processes. Manufacture of tablets is a well-known and highly-advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used. Commonly used absorbents again include starch and lactose, while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps, and polyethylene glycol.

This method of increasing the efficiency of feed utilization can also be practiced by the administration of the instant compound as a slow-pay-out bolus. Such boluses are made as tablets are made, except that a means to delay the dissolution of the compound is provided. Boluses are made to release for lengthy periods. The slow dissolution is assisted by choosing a highly water-insoluble form of the compound. A substance such as iron filings is added to raise the density of the bolus and keep it static on the bottom of the rumen.

Dissolution of the compound is delayed by use of the matrix of insoluble materials in which the drug is embedded. For example, substances such as vegetable waxes, purified mineral waxes, and water unsoluble polymeric materials are useful.

Drenches of the instant compounds are prepared most easily by choosing a water soluble or water dispersable form of the compound. If an insoluble form is desired for some reason, a suspension may be made. Alternatively, a drench may be formulated as a solution in a physiologically acceptable solvent such as a polyethylene glycol.

Suspension of insoluble forms of the compounds can be prepared in non-solvent such as vegetable oils such as peanut, corn, or sesame oil; in a glycol such as propylene glycol or a polyethylene glycol; or in water, depending on the form of the compound chosen.

Suitable physiologically acceptable adjuvants are necessary in order to keep the compound suspended. The adjuvants can be chosen from among the thickeners, such as carboxymethylcellulose, polyvinylpyrrolidone, gelatin, and the alginates. Many classes of surfactants also will serve to suspend the compounds. For example, lecithin, alkylphenol polyethylene oxide adducts, naphthalene sulfonates, alkylbenzenesulfonates and the polyoxyethylene sorbitain esters are useful for making suspension in liquid nonsolvents.

In addition, many substances which effect the hydrophilicity, density, and surface tension of the liquid can assist in making suspensions in individual cases. For example, silicone antifoams, glycols, sorbitol, and sugars can be useful suspending agents.

The suspendable compound may be offered to the animal grower as a suspension, or as a dry mixture of the compound and adjuvants to be diluted before use.

The compounds may also be administered in the drinking water of the ruminants. Incorporation into drinking water is performed by adding a water soluble or water suspendable form of desired compound to the water in the proper amount. Formulation of the compound for addition to drinking water follows the same principles as formulation of drenches.

The most practical way to treat animals with the compounds of this invention usable in this novel method is by the formulation of the compound into the feed supply. Any type of feed may be medicated with the instant compounds, including common dry feeds, liquid feeds, and pelleted feeds.

The methods of fomulating drugs into animal feeds are well known. It is usual to make a concentrated drug premix as a raw material for medicated feeds. For example, typical drug premixes may contain from about 1 to about 800 g, of drug per kg of premix. The wide range results from the wide range of concentration of drug which may be desired in the final feed. Premixes may be either liquid or solid.

The formulation of ruminant feeds containing the proper amounts of the instant compounds for useful treatment is mainly a matter of arithmetic. It is necessary only to calculate the amount of compound which it is desired to administer to each animal, to take into account the amount of feed per day which the animal eats, and the concentration of compound in the premix to be used, and calculate the proper concentration of the compound in the feed.

All of the methods of formulation, mixing, and pelleting feeds which are normally used in the ruminant feed art are entirely appropriate for manufacturing feeds containing the compounds usable in this method.

It is not intended that the scope of this invention be limited to any particular formulations or methods of administration. The invention is a method of promoting growth and increasing the efficiency of feed utilization by animals by the oral administration of certain compounds regardless of the method of administration of the compounds.

It is usual to treat economic animals, with a variety of growth promoters, disease preventives, and disease treatments throughtout their lives. Such drugs are often used in combination. The novel method may be practiced in combination with other treatments.

The following examples are presented so that the invention may be more fully understood. They are not to be construed or limitative of the invention.

EXAMPLE 1

Fermentation

1. Culture

MF141 was selected from the Merck Culture Collection for screening and received as a lyophilized preparation. This was used to prepare FVM (frozen vegetative mycelia) in YMEJ seed medium (composition is detailed in Table 1). The lyophilized preparation was aseptically transferred to the seed flask, which was incubated on a gyratory shaker, 220 rpm for 3 days at 25° C., 85% relative humidity (rh). The FVM were frozen at −75° C. in 10–15% glycerol. Secondary FVM were made from these by inoculating 1.0 ml from the FVM into YMEJ seed medium and growing at 25° C., 2 days, 220 rpm, 85% rh. These FVM were frozen at −75° C. as above.

2. Seed

YMEJ seed cultures of MF141 were inoculated from 1.0 ml of the secondary FVM, and grown on a gyratory shaker (220 rpm) for 2 days at 25° C., 85% rh.

3. Initial Production (static fermentation)

The composition of the static NPF-2 production medium, in which activity was first detected, is shown in Table 1. A portion of the seed (18.0 ml) was used to inoculate the liquid component of the production medium. This flask was swirled vigorously and its contents dispensed by pouring into a vermiculite-containing 4 L roller (culture) bottle. The contents of the roller bottle were shaken/mixed to insure homogeneous inoculation and coverage. The roller bottle was incubated horizontally, revolving at approximately 4 rpm on a Wheaton roller apparatus, at 25° C. 75% rh for 20 days.

TABLE 1

| Composition of Seed and Production Media YMEJ SEED MEDIUM | |
|---|---|
| Component | g/L |
| Yeast extract | 4.0 |
| Malt extract | 8.0 |
| Dextrose | 4.0 |
| Junlon | 1.5 |

4. Improved Production (liquid medium development)

The composition of the liquid medium GG1 (for improved unguinol production) is shown in Table 2. Seed cultures were inoculated as described above (section 2) and grown at 220 rpm on a gyrotary shaker for 1 day at 25° C. 85% rh. An aliquot of the seed (1.5 ml) was used to inoculate each production flask, containing 50 ml (3% inoculum). Flasks were incubated on a gyratory shaker (220 rpm) for 18 days at 25° C. 85% rh.

The medium was prepared with distilled water and the pH adjusted to 7.0 prior to sterilization. The medium was dispensed at 54 ml/250 ml plain Erlenmeyer flask. Cotton closures were used. Sterilization was at 121° C. for 20 minutes.

| NPF-2 PRODUCTION MEDIUM Liquid Portion | |
|---|---|
| Component | g/L |
| Glucose | 150.0 |
| Urea | 4.0 |
| N Z amine type A | 4.0 |
| $K_2HPO_4$ | 0.5 |
| $MgSO_4.7H_2O$ | 0.25 |
| KCl | 0.25 |
| $ZnSO_4.7H_2O$ | 0.9 |
| $CaCO_3$ | 16.5 |

The medium was prepared with distilled water (no pH adjustment). 425 ml was dispensed for each 1 liter plain Erlenmeyer flask. The flasks were closed with cotton and autoclaved at 121° C. for 15 minutes.

TABLE 2

| Compositin of GG1 Liquid Production Media | |
|---|---|
| Component | g/L |
| Glycerol | 75.0 |
| Glucose | 10.0 |
| Ardamine pH | 5.0 |
| $(NH_4)_2SO_4$ | 2.0 |
| Soybean meal | 5.0 |
| Tomato paste | 5.0 |
| Sodium Citrate | 2.0 |

The medium was prepared with distilled water and the pH adjusted to 7.0 prior to sterilization. The medium was dispensed at 54 ml/250 ml plain Erlenmeyer flask. Cotton closures were used. Sterilization was at 121° C. for 20 minutes.

Solid Portion

Add 1250 cc vermiculite to a 4 L roller (culture) bottle. Plug with latex closure; autoclave for 1 hr. on wrapped goods cycle and 30 min. dry.

EXAMPLE 2

Isolation of Unguinol and Folipastatin

This 2 L solid fermentation batch of *Aspergillus Unguis*, was extracted with 4 L of methyl ethyl ketone, shaken for 1 hr, and evaporated in vacuo to an aqueous mixture. The aqueous concentrate of the methyl ethyl ketone extract was extracted with 0.5 L of hexanes followed by 0.5 L of methylene chloride. The two extracts were pooled and dried to give 6 g of tan powder.

Five grams of dried extract, dissolved in 25 mL of ethyl acetate/methylene chloride 1:1, was applied to a column of silica gel (E. M. Kieselgel 60, 450 mL) and eluted with hexanes/ethyl acetate 2:1. All the active fractions were monitored by TLC (Silica, hexanes: ethyl acetate 2:1). Fractions eluting between 2.0 and 2.5 column volumes were pooled to give a rich-cut with an $R_f=0.25$ which was identified as folipastatin. Fractions eluting between 2.5 and 3.8 column volumes were pooled to give a rich-cut of unguinol ($R_f=0.23$).

The first fraction with an Rf of 0.25 was further purifed by dissolving in 5 mL of methylene chloride and precipitating by the dropwise addition of hexanes. Over 80 mg of 95% pure compound was obtained. The purity was determined by RP HPLC (Whatman.ODS-3, 10×4.6, 225 nm, 1.0 mL/min, 35° C., methanol/water 60:40) with a Rt of 23 mins. (12 mins for Unguinol). Extensive spectroscopic data including 2D NMR was obtained on this material. A tentative identification as folipastatin was established at this point by comparison to published data (Hamaro et al., *J. Antibiotics* pg 1195–1201 (1992)).

Crystallization of folipastatin occurred by dissolving 60 mg of above material in 1 mL of methanol and leaving the solution at room temperature overnight. A portion of these crystals were used for final structure confirmation by X-ray diffraction which resulted in the structure given above.

The unguinol rich-cut from the silica gel fractionation ($R_f=0.23$) was purified by a parallel method. Precipitation from methylene chloride/hexanes provided 1.2 g of compound. A portion of this material was crystallized from methanol to yield 97% pure unguinol. The structure was established by comparison to published spectral data and X-ray diffraction.

EXAMPLE 3

Isolation of 2-Chloro Unguinol and 4-Methyl Unguinol

A 100 mL sample of the mother liquors from the unguinol crystallization of Example 2 was dried and dissolved in 100 mL of 1:1, hexanes:ethyl acetate. This solution was applied to a column of silica gel (E. M. Kieselgel 60, 1 L) which was developed with 4:1, Hexanes:ethyl acetate for 1 column volumn followed by 9 column volumns of 3:1, Hexanes:ethyl acetate. Fractions eluting from 4.0 to 5.0 column volumns were pooled to give a rich cut of 2-chloro unguinol (TLC, Silica gel; 2:2:1, hexanes:methylene chloride:ethyl acetate; $R_f=0.7$). Fractions eluting from 6.0 to 7.0 column volumns were pooled to give a rich cut of 4-methyl unguinol (TLC, Silica gel; 2:2:1, hexanes:methylene chloride:ethyl acetate; $R_f=0.65$).

The 2-choro unguinol was further purified by repetitive preparative HPLC (Whatman ODS-3, 2.25×25 cm; 61:39, methanol:water, 10 mL/min; 225 nm). The 2-choro unguinol that eluted between 65 and 75 minutes was collected by evaporation of the pure fractions. The structure was determined by comparison of $^1H$ and $^{13}C$ NMR as well as MS data to that previously published for this compound.

The 4-methyl unguinol was further purified by repetitive preparative HPLC (Whatman ODS-3, 2.25×25 cm; 61:39, methanol:water, 10 mL/min; 225 nm). The 4-methyl unguinol that eluted between 55 and 68 minutes was collected by evaporation of the pure fractions. Structure elucidation for this Compound was based upon $^1H$ and $^{13}C$ NMR as well as MS analysis. Several 2D NMR techniques such as nuclear overhauser enhancement, correlation of spectroscopy, heteronuclear multiquantum coherence and heteronuclear multibond coherance were also employed to establish the structure.

What is claimed is:

1. A method for promoting the growth of animals and for increasing the efficiency of feed utilization of such animals which comprises administering to such animals an effective amount of unguinol, or derivatives thereof having the following structures:

UNGUINOL

-continued

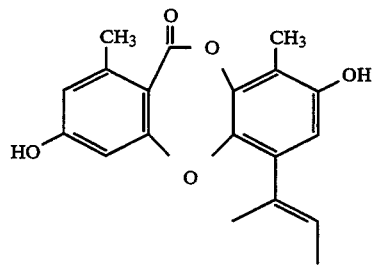

FOLIPASTATIN

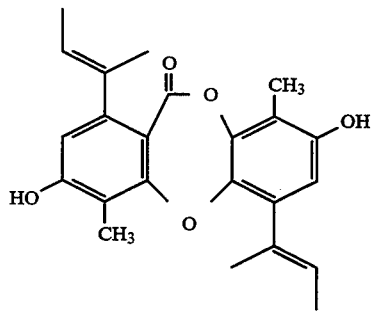

4-METHYL UNGUINOL

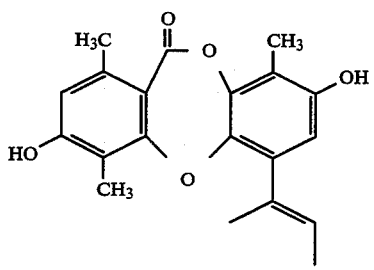

-continued

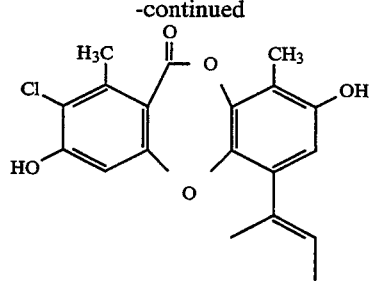

or mixtures thereof.

2. The method of claim 1 where the compound is unguinol.

3. The method of claim 1 where the compound is folipastatin.

4. The method of claim 1 where the compound is 2-chloro unguinol.

5. The method of claim 1 where the compound is 4-methyl unguinol.

6. A composition for promoting the growth of animals and for increasing the efficiency of feed utilization of such animals which comprise a carrier and an effective amount of unguinol derivative having the following structure:

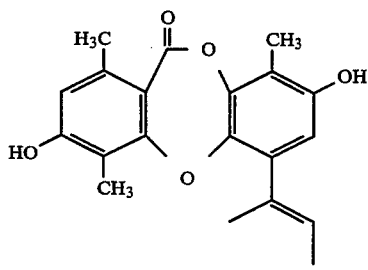

7. A compound having the formula

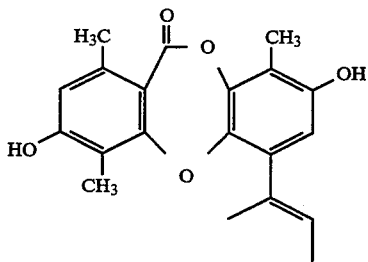

which is 4-methyl unguinol.

* * * * *